United States Patent [19]

Rosenthal

[11] Patent Number: 4,734,584
[45] Date of Patent: Mar. 29, 1988

[54] QUANTITATIVE NEAR-INFRARED MEASUREMENT INSTRUMENT FOR MULTIPLE MEASUREMENTS IN BOTH REFLECTANCE AND TRANSMISSION MODES

[75] Inventor: Robert D. Rosenthal, Gaithersburg, Md.

[73] Assignee: Trebor Industries, Inc., Gaithersburg, Md.

[21] Appl. No.: 907,889

[22] Filed: Sep. 16, 1986

[51] Int. Cl.⁴ ............................................. G01J 1/00
[52] U.S. Cl. ................................ 250/343; 250/358.1; 250/428
[58] Field of Search ............... 250/343, 344, 349, 428, 250/358.1; 356/437, 436, 440, 244, 73

[56] References Cited

U.S. PATENT DOCUMENTS

| | | | |
|---|---|---|---|
| 3,344,702 | 10/1967 | Wood et al. | 356/440 |
| 3,910,701 | 10/1975 | Henderson et al. | 356/73 |
| 4,125,328 | 11/1978 | Suga | 356/73 |
| 4,171,909 | 10/1979 | Kramer et al. | 356/73 |
| 4,281,248 | 7/1981 | Fabinski et al. | 250/343 |
| 4,479,058 | 10/1984 | Gast et al. | 356/73 |
| 4,602,160 | 7/1986 | Mactaggart | 356/73 |

OTHER PUBLICATIONS

Rosenthal, "Characteristics of Non-Destructive Near-Infrared Instruments for Grain and Food Products", 1985 Meeting of Japan Food Science Institute, pp. 1–23.

Primary Examiner—Janice A. Howell
Assistant Examiner—William F. Rauchholz
Attorney, Agent, or Firm—Bernard, Rothwell & Brown

[57] ABSTRACT

A near-infrared quantitative measurement instrument allows measurement in either reflectance or transmission modes depending upon a sample holder which is loaded in a sample chamber. The instrument has means for detecting in both the reflectance mode and the transmission mode, and the particular sample holder used determines in which mode the measurement is made.

7 Claims, 2 Drawing Figures

U.S. Patent    Mar. 29, 1988    4,734,584
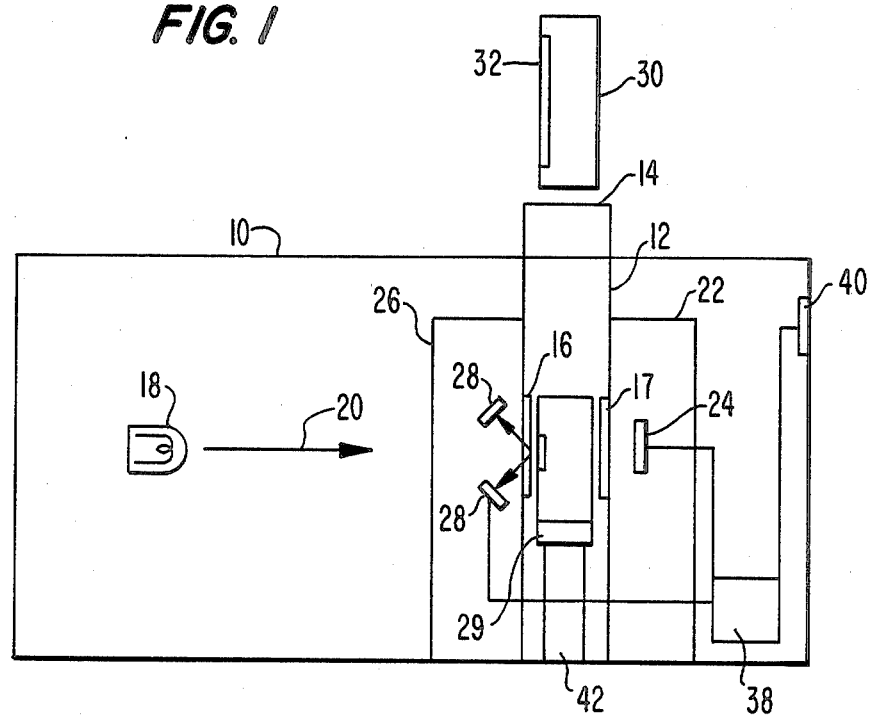
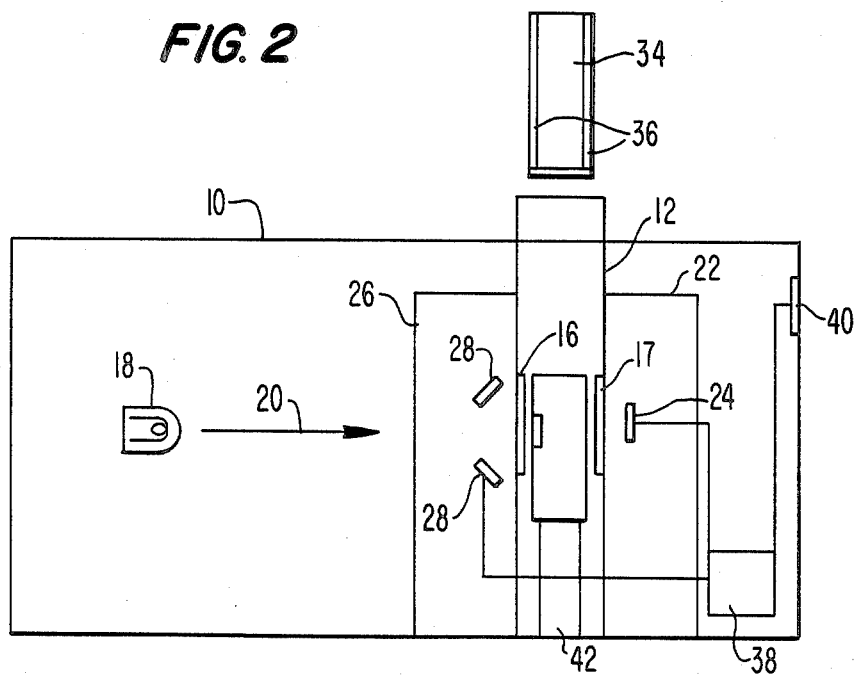

QUANTITATIVE NEAR-INFRARED MEASUREMENT INSTRUMENT FOR MULTIPLE MEASUREMENTS IN BOTH REFLECTANCE AND TRANSMISSION MODES

BACKGROUND OF THE INVENTION

1. Field of the Invention

This invention relates to improvements in near-infrared quantitative measurements instruments and particularly to a novel NIR quantitative measurement instrument capable of measurements in both reflectance and transmission modes.

2. Prior Art

In the early 1970's, quantitative near-infrared (NIR) instruments were introduced to satisfy the need for rapid accurate measurements of nutritional constituents within grain and oil seeds. In the fifteen or so years since their introduction, near-infrared instruments have proven their ability to provide fast, accurate measurements of protein, oil, moisture and other constituents in a wide variety of these applications. The capability of these instruments have led to their widespread use in qualitative control functions in the grain industry. Specifically, thousands of these instruments are currently used in measuring protein and moisture in wheat and barley.

There are two general types or categories of near-infrared instruments currently on the market: (1) those that make measurements by reflecting light off of a ground sample, and (2) those that make measurements by transmitting light directly through an unground sample. Thus, these instruments act in the reflectance and the transmission modes respectively.

Certain available commercial instruments have the ability of changing from a reflectance measurement mode to a transmission measurement mode but only by making hardware modifications which are both time consuming and subject to operator error.

Furthermore, in the measurement of certain types of products, e.g. mixed feed, forages, or whole grains, measurement of a very large sample is desirable to average out the non-homogeneous content of the sample. In the known commercial instruments the methods used to measure large ground samples include the use of a spinning sample cup which is located eccentrically relative to a light beam, i.e., the NIR optical axis. This approach allows the NIR beam to illuminate a larger area as the cup is rotated. However, in instruments having a rotating sample cup, it is difficult to remove it in order to convert the instrument to a transmission measurement mode which many users prefer for whole grain measurement. There is a significant need in the art to make both transmission and reflectance measurements at multiple positions of a sample without any hardware modifications whatsoever.

SUMMARY OF THIS INVENTION

This invention provides a single instrument which can be used in both the reflectance and transmission modes for NIR quantitative measurements. This invention includes the unique sample handling system which together with the instrument allows immediate change from a transmission measurement mode to a reflectance measurement mode without any changes to the instrument hardware for the sample system. The only change is in the type of sample holder placed in the instrument.

The instrument includes a sample chamber which is hollow for receiving a sample holder. The sample chamber is sandwiched between a reflectance detection chamber and a transmission detection chamber with appropriate NIR radiation being directed to the sample chamber along an optical axis. Alternate sample holders are used depending on whether the instrument is to be used in a reflectance mode or the transmission mode. For reflectance measurement a sample holder has a window on only one side, the side nearest the optical axis and the reflectance chamber so that the NIR may be reflected off the sample, detected and the signals processed and then displayed to indicate the measurement. For operating in the transmission mode, a separate sample holder is utilized having windows on both sides so that the appropriate NIR radiation is detected in the transmission detection chamber, the signals processed and the measurements displayed.

BRIEF DESCRIPTION OF THE DRAWINGS

FIG. 1 is a schematic view of the instrument of this invention utilized with a sample holder for measurements in the reflectance mode.

FIG. 2 is a similar schematic view utilized with an alternate sample holder for measurements in a transmission mode.

DETAILED DESCRIPTION OF THE PREFERRED EMBODIMENT

A near-infrared instrument includes a housing 10 containing a hollow sample chamber 12. The sample chamber 12 is open at the top 14 for the insertion of a sample holder. The walls of the sample chamber may be of any material, preferably material which is opaque to NIR radiation except for windows 16 and 17 in opposite sides thereof. Window 16 is of near-IR-quartz which has negligible absorption through 2,600 nm. Window 17 is an optically transparent material with negligible absorption through 1,100 nm. Window 17 also contains a metal mesh that transmits most of the optical energy (over 80%) and yet absorbs most electro-magnetic waves that might interfere with the transmission detection.

A source of NIR radiation 18 is directed by any suitable means along an optical axis 20 toward the windows 16 and 17 of the sample chamber 12.

Positioned on one side of the sample chamber 12, the side opposite the radiation source, is a transmission detection chamber means in the form of a chamber 22 having a detector or pickup 24 therein for detecting certain NIR wave lengths transmitted through the sample chamber.

On the other side of the sample chamber, nearest the source of radiation, is a reflectance means or chamber 26 having a reflectance detector 28. A removable reflectance reference standard 29 is left in the sample chamber 12 during reflectance measurements. The reflectance standard may be that disclosed in co-pending application Ser. No. 907,890 filed Sept. 16, 1986, namely, a unique pressed variation of the Halon standard recommended by the National Bureau of Standards (NBS).

A sample holder 30 (shown schematically) is of the type used for reflectance and has a near-IR-quartz window 32 on the side thereof that is placed closest to the reflectance detection chamber 26. The sample holder 30 is otherwise constructed of IR-opaque material. It is inserted into sample chamber 12 and rests on top of reflectance standard 29.

For operating in the transmission mode, the reflectance standard 29 is removed. The transmission sample holder 34, FIG. 2, has near-IR transmitting plastic windows 36 in both sides thereof as disclosed in my aforesaid application Ser. No. 739,679 now U.S. Pat. No. 4,692,620. In addition, the sample chamber 12 may be generally as disclosed in my prior application Ser. No. 739,679, now U.S. Pat. No. 4,692,620, which discloses mechanical means 42 for moving the sample holder such as a way of obtaining multiple readings of the same sample by moving the sample chamber. Signals processed by the detectors in the detection chambers are fed to and processed by a computer 38 and may then be displayed on a readout 40 at the front of the instrument.

The instrument may operate without technically-trained users. A reflectance measurement is performed by inserting a ground sample into sample holder 30 and putting the sample holder 30 into the sample chamber 12, where the reflectance standard 29 had previously been inserted. When a light protecting hood (not shown) is closed, the instrument starts and scans the standard 29 and then the mechanical system 42 lowers the standard 29 thereby lowering the sample holder 30 in the IR-energy beam to provide the measurement.

Transmission measurements are made in a somewhat similar and related fashion. That is, the sample (in this case usually unground grain) is placed in the sample holder 34 and the sample holder is placed in the sample chamber 12. Again, the light protecting hood is closed and the instrument automatically scans the sample. For transmission measurements, there is no need to utilize the reflectance standard and it is removed from the instrument. The "standard" used for transmission measurements is the air of an empty sample chamber. This is appropriate since air has essentially no absorptions in the 600 to 1,100 nm transmission measurement region utilized in the instrument.

The invention has been recently incorporated into a commercially available instrument known as the TREBOR-70. In the preferred embodiment there is a high-energy single beam source of IR energy generated by having light from a tungsten halogen bulb pass through a restrictive aperture and strike a 90 nm holographic grating and then pass through an exit aperture. All other optics (e.g. lenses, plates) are near-infrared quartz. The reflectance geometry is NBS-recommended 0°–45° illuminent/detector and the reflectance detectors are four lead sulfide detectors. The transmittance detectors are of enhanced silicon. The wave length range of the instrument in normal use is 600 to 1,100 nm for transmittance and 1,100 through 2,500 nm in reflectance but can be extended to a range of 500 to 2,600 nm. In operation, the scan time is less than 30 seconds in either the reflectance or transmittance modes. The wave length accuracy is 0.5 nm and the wave length repeatability is less than 0.015 nm S.D. The effective sample area is illumination in oblong shape over a 12.5 square centimeter area. The linearity is one percent of the reading. The currently used construction allows up to four different parts of the samples to be measured in the reflectance mode, and up to eighteen different parts of the samples to be measured in the transmission mode (the number of readings in each mode depends upon the non-homogeneity of the sample).

As can be seen, the invention disclosed is a new generation in near-IR quantitative measurement allowing the utilization of a single instrument for both reflectance and transmission measurement modes thus greatly increasing the versatility and range of use of the instrument.

I claim:

1. An instrument for making quantitative measurements of a sample using near-infrared radiation and detectors therefor, the instrument being capable of making such measurements by either transmission through the sample or reflectance from the sample, the instrument comprising:
    (a) a housing member,
    (b) a sample chamber within the housing, the sample chamber having near-infrared transparent windows therein and being hollow and capable of accepting removable sample holders,
    (c) a source of near-infrared radiation directed on an optical axis toward the sample chamber and normally passing through the NIR-transparent windows of the sample chamber,
    (d) an NIR transmission detection means on the side of the sample chamber opposite the source of NIR radiation,
    (e) an NIR reflectance detection means on the same side of the sample chamber as the source of NIR radiation,
    (f) a first sample holder means for insertion into the sample chamber and adapted to hold and position a sample therein a condition specifically suited to the reflection of the NIR radiation from a surface thereof for the measurement of the magnitude of such reflection; and
    (g) a second sample holder means for insertion into the sample chamber and adapted to allow transmission of the NIR radiation therethrough and to hold and position a sample therein in a condition specifically suited to the transmission of the NIR radiation through the sample and the measurement of the magnitude of such transmission.

2. An instrument as in claim 1 wherein the first sample holder means includes NIR-radiation-transparent windows on one side only so that NIR radiation will not pass through the chamber and will be reflected from the surface thereof, and the second sample holder means includes NIR-radiation-transparent windows on opposite sides thereof along the optical axis so that NIR radiation will pass through the sample holder.

3. An instrument as in claim 2 wherein all windows of the sample holders and sample chamber are near-infrared quartz.

4. An instrument as in claim 3 further comprising wire mesh on a window in front of a silicon detector that passes most near-IR energy and yet absorbs most electro-magnetic energy that would interfere with the detector's signal.

5. An instrument as in claim 2 further comprising means for moving at least one of sample holders within the sample chamber during measurement thereon.

6. An instrument as in claim 2 further comprising a reflectance standared for use with the NIR reflectance detection means.

7. An instrument as in claim 6 wherein the reflectance standard is moved by a sample holder moving means for alternately moving the reflectance standard or at least one of the sample holders onto the optical axis.

* * * * *